United States Patent [19]

Cousse et al.

[11] Patent Number: 4,605,654

[45] Date of Patent: Aug. 12, 1986

[54] 2-(ARYLALKYLOXYMETHYL)MORPHOLINES AND THE CENTRAL NERVOUS SYSTEM COMPOSITIONS

[75] Inventors: Henri Cousse; Gilbert Mouzin; Jean-Pierre Rieu; Mike Briley; Antoine Stenger, all of Castres, France

[73] Assignee: P. F. Medicament, Paris, France

[21] Appl. No.: 809,698

[22] Filed: Dec. 17, 1985

[30] Foreign Application Priority Data

Dec. 20, 1984 [FR] France .................. 84 19553

[51] Int. Cl.⁴ .................. A61K 31/535; C07D 295/08; C07D 413/12
[52] U.S. Cl. .................. 514/237; 544/148; 544/165; 544/167; 544/174; 544/177; 514/238; 514/240
[58] Field of Search .................. 544/148, 165, 167, 174, 544/177; 514/237, 238, 240

[56] References Cited

U.S. PATENT DOCUMENTS 3,714,161  1/1973  Blakeney et al. .................. 544/174

Primary Examiner—Robert W. Ramsuer
Attorney, Agent, or Firm—Fulbright & Jaworski

[57] ABSTRACT

The present invention relates to new 2-(arylalkyloxymethyl)morpholine derivatives, the preparation thereof and their application as drugs which are useful in the treatment of disorders of the central nervous system.

The 2-(arylalkyloxymethyl)morpholine derivatives according to the invention correspond to the general formula (I):

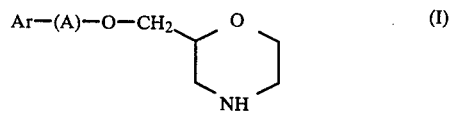

in which: Ar denotes an aromatic group and more especially the following radicals:

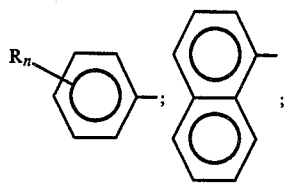

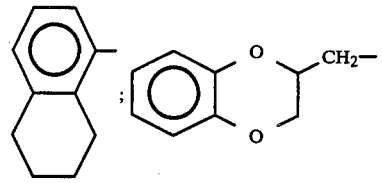

in the case where Ar denotes a phenyl radical and R denotes a hydrogen atom, an alkyl, alkoxy or halogen group, a trifluoromethyl radical, a nitro or amino group, a hydroxy group or an arylalkyloxy group.

3 Claims, No Drawings

2-(ARYLALKYLOXYMETHYL)MORPHOLINES AND THE CENTRAL NERVOUS SYSTEM COMPOSITIONS

The present invention relates to new 2-(arylalkyloxymethyl)morpholine derivatives possessing broad-spectrum antidepressant properties, the process for preparation thereof and their application as drugs which are useful in the treatment of disorders of the central nervous system.

In French Patent A-2,479,822, an original method is reported whereby access is readily gained to high yields of arylalkoxyglycidyl ethers of general formula A;

This original method formed the subject of the following publication: "A convenient one-step synthesis of glycidyl ethers" by G. MOUZIN, H. COUSSE, J. P. RIEU and A. DUFLOS in Synthesis, Feb. 1983, p. 117.

These epoxydes were used for synthesizing arylalkoxypropanolamines (B) described in French Patent A-2,479,814. These derivatives possess surprising β-blocking properties which are useful in the treatment of cardiovascular disorders:

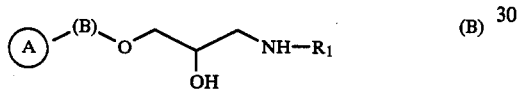

Since some arylalkoxypropanolamine derivatives had also shown pharmacological properties on the central nervous system, it appeared useful to study the pharmacological activity of these derivatives cyclized to morpholine form.

Some morpholines substituted at position 2 have already been described as showing antidepressant properties, and more especially the derivatives of formulae:

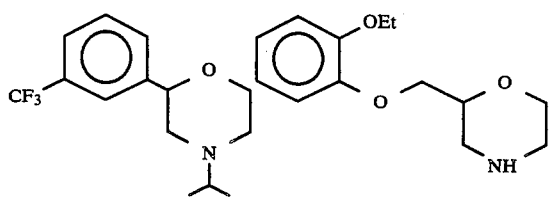

OXAFLOZANE          VILOXAZINE

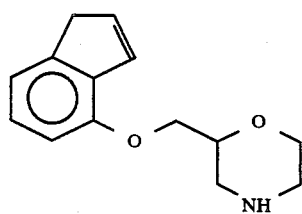

YM 08054-1

The compounds discovered by the Applicant, which show a structural difference at the level of the link with the aromatic ring, in the form of the presence of a carbon-containing group, show, in comparison with the abovementioned derivatives, specific antidepressant properties.

These molecules potentiate the action of 5-HTP according to the method of CHRISTENSEN A. V. et al., Eur. J.Pharmacol.1977,41, 153–162. In contrast, these compounds prove inactive in the test of 5-HT uptake according to the method of LANGER et al. (Science,1980,210,1133–1135). This suggests an indirect mechanism of action, favoring the serotoninergic system.

The subject of the invention is 2-(arylalkyloxymethyl)morpholines of general formula (I):

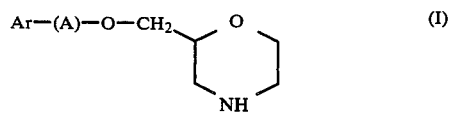

in which:

Ar denotes an aromatic group, and more especially the following radicals:

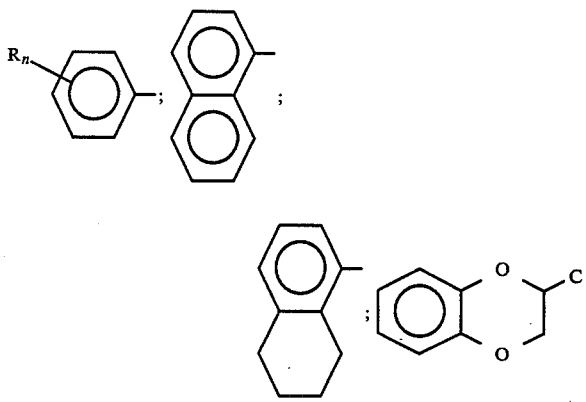

In the case where Ar denotes a phenyl radical, R denotes a hydrogen atom, an alkyl, alkoxy or halogen group, a trifluoromethyl radical, a nitro or amino group, a hydroxy group or an arylalkyloxy group, n denotes the values 1, 2, 3;

in the case where n=2 or 3, the radicals R can be identical or different, or can form in pairs a methylenedioxy or 1,2-ethylenedioxy group; and A denotes a linear or branched alkylene radical having 1 to 4 carbon atoms or an alkenylene radical having 2 to 3 carbon atoms.

The present invention also relates to the salts of the compounds of formula (I) with therapeutically acceptable inorganic or organic acids.

Throughout the text of the present Application, alkyl fragments preferably denote linear or branched radicals containing from 1 to 4 carbon atoms.

The present invention also relates to a process for preparing the derivatives of formula (I), by reacting the epoxydes of formula (II):

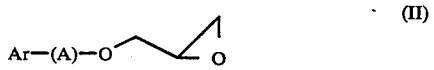

in which Ar and (A) have the same meaning as in formula (I), with 2-aminoethyl hydrogen sulfate (ester) in an aqueous alcoholic solvent such as, for example, an ethanol-water or methanol-water mixture, according to the synthetic scheme:

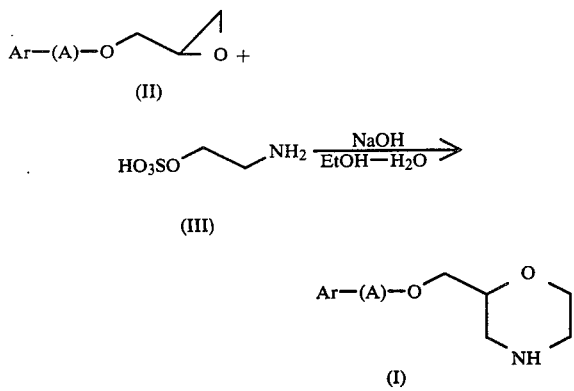

The epoxide of formula (II) can be prepared by the reaction of epichlorohydrin with an alcohol of formula (IV):

where Ar and (A) have the same meaning as above, in the presence of a strong base such as sodium hydroxide and a catalyst such as tetrabutylammonium hydrogen sulfate, as described in French Patent No. A-2,479,822.

The present invention likewise relates to the use of the compounds of formula (I) by way of a drug, as well as the pharmaceutical compositions containing these drugs.

Pharmaceutical compositions according to the present invention can contain 1 or more compounds of formula (I), optionally in combination with other active principles.

Among the derivatives of formula (I), the following derivatives may be mentioned more especially:
2-(benzyloxymethyl)morpholine hydrogen maleate
2-[(2-methoxybenzyloxy)methyl]morpholine hydrogen maleate
2-[(3-methoxybenzyloxy)methyl]morpholine hydrogen maleate
2-[(4-methoxybenzyloxy)methyl]morpholine hydrogen oxalate
2-[(2-methylbenzyloxy)methyl]morpholine hydrogen maleate
2-[(3-methylbenzyloxy)methyl]morpholine hydrogen maleate
2-[(4-methylbenzyloxy)methyl]morpholine hydrogen oxalate
2-[(2-chlorobenzyloxy)methyl]morpholine hydrogen maleate
2-[(3-chlorobenzyloxy)methyl]morpholine hydrogen maleate
2-[(4-chlorobenzyloxy)methyl]morpholine hydrogen maleate
2-[(2-ethoxybenzyloxy)methyl]morpholine hydrogen maleate
2-[(2,4-dichlorobenzyloxy)methyl]morpholine hydrogen maleate
2-[(2,6-dichlorobenzyloxy)methyl]morpholine hydrogen maleate
2-[(2-fluoro-6-chlorobenzyloxy)methyl]morpholine hydrogen maleate.

The examples which follow illustrate the preparation of some derivatives according to the present invention without, of course, limiting the scope thereof.

EXAMPLE 1

2-(benzyloxymethyl)morpholine hydrogen maleate (1a) 1-Benzyloxy-2,3-epoxypropane In a 500-ml three-necked flask, a mixture consisting of 100 ml of 50% strength caustic soda solution, 100 ml of epichlorohydrin (1.25 mol) and 3.4 g (0.01 mol or 4 moles percent) of tetrabutylammonium hydrogen sulfate is treated dropwise with 27 g (0.25 mol) of benzylalcohol, stirring vigorously.

The addition, which lasts half an hour, is carried out in such a way that the temperature does not exceed 25°, the three-necked flask being immersed if necessary in a cold water bath.

The stirring is continued for a further 2 hours. The mixture is treated with 200 ml of cold water. The organic phase is decanted, the aqueous phase is extracted with twice 100 ml of methylene chloride and the organic phases are combined.

After the organic phases are washed with 5% strength bicarbonate solution and with water, and dried over sulfate, the solvent and excess epichlorohydrin are driven off in a rotary evaporator and the residual oil is distilled under vacuum.

B.p.: 80°–85°/0.4; Yld: 91% of 1-benzyloxy-2,3-epoxypropane.

(1b) 2-(Benzyloxymethyl)morpholine hydrogen maleate 130 g (0.94 mol) of 2-aminoethyl hydrogen sulfate (ester) are added in the course of 10 minutes to 45 ml of 40% strength caustic soda. After a further 10 minutes' stirring, the above mixture is treated with a solution of 20 g (0.121 mol) of the above epoxide in 90 ml of methanol. The medium is brought to reflux for 1 h, 45 ml of 40% strength caustic soda are then added and the mixture is brought to reflux for a further 8 h.

After being left overnight at room temperature, the mixture is poured into 250 ml of water and 250 ml of toluene, stirring vigorously. The organic phase is separated, the aqueous phase re-extracted with toluene and the toluene phases combined.

The organic phase is treated with 2×150 ml of 2N sulfuric acid. The organic base is sorted out of the acidic aqueous phase by adding caustic soda to pH 14, and extracted with 2×100 ml of toluene. The organic phase is washed with saline water, dried over sulfate and then evaporated to dryness. The above oily base (20.4 g), dissolved in 50 ml of isopropyl alcohol, is added to a solution of 11.5 g of maleic acid in 100 ml of the same solvent brought to boiling.

After a slight amount of insoluble material is filtered off hot, the product is left to crystallize slowly for 24 h at room temperature, and the derivative of formula:

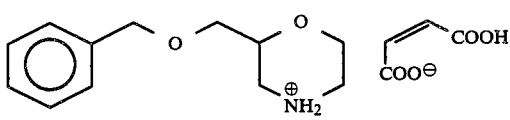

is recovered in 40% yield.
Empirical formula: $C_{16}H_{21}NO_6$
Molecular mass: 323.353

Melting point: 111°
Thin layer chromatography:
  support: silica gel Merck 60 F 254
  solvent: chloroform/methanol/ammonia 90:9:1
  visualization: UV, iodine
  Rf: 0.35
Solubility: soluble to 10% in water.

EXAMPLE 2

2-[(2-Methoxybenzyloxy)methyl]morpholine hydrogen fumarate

From o-methoxybenzyl alcohol, the procedure of Example (1a) being applied, 1-(ortho-methoxybenzyloxy)-2,3-epoxypropane is obtained. When condensed according to the procedure of Example (1b), this derivative leads, after salification with fumaric acid, to the derivative of formula:

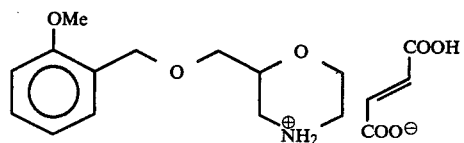

Empirical formula: $C_{17}H_{23}NO_7$
Molecular mass: 353.37
Melting point: 128°
Thin layer chromatography:
  support: silica gel Merck 60 F 254
  solvent: chloroform/methanol/ammonia (80:18:2)
  visualization: UV and iodine
  Rf: 0.63
Solubility: soluble to 5% in water.

EXAMPLE 3

2-[(3-Methoxybenzyloxy)methyl]morpholine hydrogen maleate

From meta-methoxybenzyl alcohol, the procedure of Example (1a) being applied, 1-(meta-methoxybenzyloxy)-2,3-epoxypropane is prepared. When condensed according to the procedure described in Example (1b), this derivative leads to the derivative of formula:

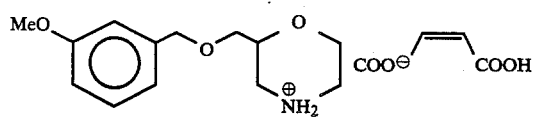

Empirical formula: $C_{17}H_{23}NO_7$
Molecular mass: 353.37
Melting point: 102°
Thin layer chromatography:
  support: silica gel Merck 60 F 254
  solvent: chloroform/methanol/ammonia solution (90:9:1)
  visualization: UV and iodine
  Rf: 0.4
Solubility: soluble to 1% in water.

EXAMPLE 4

2-[(4-methoxybenzyloxy)methyl]morpholine hydrogen oxalate

The procedure of Example (1a) being used, with benzyl alcohol replaced by para-methoxybenzyl alcohol, the intermediate epoxide 1-(para-methoxybenzyloxy)-2,3-epoxypropane is obtained. When condensed with 2-aminoethyl hydrogen sulfate according to Example (1b), this epoxide leads, after salification with oxalic acid, to the derivative of the following structure:

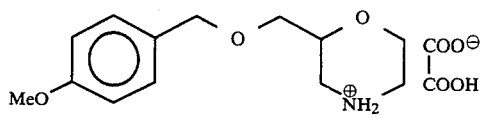

Empirical formula: $C_{15}H_{21}NO_7$
Molecular mass: 327.33
Melting point: 119°
Thin layer chromatography:
  support: silica gel Merck 60 F 254
  solvent: chloroform/methanol/ammonia solution (80:18:2)
  visualization: UV and iodine
  Rf: 0.65
Solubility: soluble to 4% in water.

EXAMPLE 5

2-[(2-Methylbenzyloxy)methyl]morpholine hydrogen maleate

The procedure of Example (1a) being used, with benzyl alcohol replaced by ortho-methylbenzyl alcohol, the intermediate epoxide 1-(ortho-methylbenzyloxy)-2,3-epoxypropane is obtained. When condensed with 2-aminoethyl hydrogen sulfate (ester) according to Example (1b), this derivative leads to the derivative of structure:

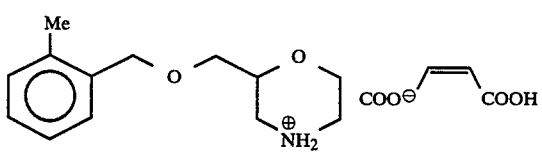

Empirical formula: $C_{17}H_{23}NO_6$
Molecular mass: 337.372
Melting point: 120°
Thin layer chromatography:
  support: silica gel Merck 60 F 254
  solvent: chloroform/methanol/ammonia solution (80:18:2)
  visualization: UV and iodine
  Rf: 0.63.

EXAMPLE 6

2-[(3-Methylbenzyloxy)methyl]morpholine hydrogen maleate

With benzyl alcohol replaced by meta-methylbenzyl alcohol in the procedure of Example (1a), the intermediate epoxide 1-(meta-methylbenzyloxy)-2,3-epoxypropane is obtained. The latter derivative, when condensed with 2-aminoethyl hydrogen sulfate, leads according to Example (1b) to the derivative of formula:

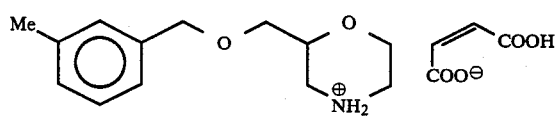

Empirical formula: $C_{17}H_{23}NO_6$
Molecular mass: 337.372
Melting point: 124° C.
Thin layer chromatography:
  support: silica gel Merck 60 F 254
  solvent: chloroform/methanol/ammonia solution (80:18:2)
  visualization: UV and iodine
  Rf: 0.68
Solubility: soluble to 3% in water.

EXAMPLE 7

2-[(4-Methylbenzyloxy)methyl]morpholine hydrogen oxalate

The procedure of Example (1a) being used, with benzyl alcohol replaced by para-methylbenzyl alcohol, the corresponding 1-(para-methylbenzyloxy)-2,3-epoxypropane is obtained. When condensed with 2-aminoethyl hydrogen sulfate, this derivative leads according to Example (1b), after salification with oxalic acid, to the derivative of formula:

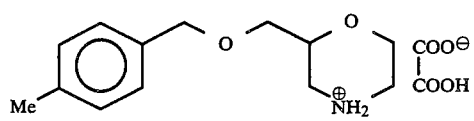

Empirical formula: $C_{15}H_{21}NO_6$
Molecular mass: 311.334
Melting point: 99° C.
Thin layer chromatography:
  support: silica gel Merck 60 F 254
  solvent: chloroform/methanol/ammonia solution (80:18:2)
  visualization: UV and iodine
  Rf: 0.65
Solubility: soluble to 2% in water.

EXAMPLE 8

2-[(2-Chlorobenzyloxy)methyl]morpholine hydrogen maleate

Application of the procedure of Example (1a) to ortho-chlorobenzyl alcohol leads to 1-(2-chlorobenzyloxy)-2,3-epoxypropane. When condensed according to Example (1b) with 2-aminoethyl hydrogen sulfate (ester), this derivative leads to the compound of formula:

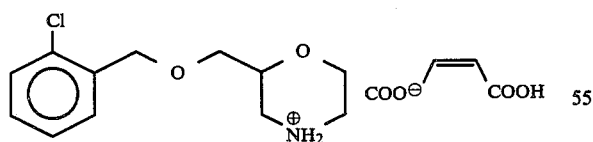

Empirical formula: $C_{16}H_{20}ClNO_6$
Molecular mass: 357.79
Melting point: instantaneous 152° C.; slow 134° C.
Slab chromatography:
  support: silica gel Merck 60 F 254
  solvent: chloroform/methanol/ammonia solution (80:18:2)
  visualization: UV and iodine
  Rf: 0.63
Solubility: soluble to 2% in water.

EXAMPLE 9

2-[(3-Chlorobenzyloxy)methyl]morpholine hydrogen maleate

The procedure of Example (1a) being applied to meta-chlorobenzyl alcohol, 1-(meta-chlorobenzyloxy)-2,3-epoxypropane is obtained. The condensation of this derivative with 2-aminoethyl hydrogen sulfate leads according to Example (1b) to the compound of formula:

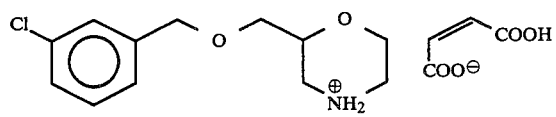

Empirical formula: $C_{16}H_{20}ClNO_6$
Molecular mass: 357.79
Melting point: 132° C.
Thin layer chromatography:
  support: silica gel Merck 60 F 254
  solvent: chloroform/methanol/ammonia solution (80:18:2)
  visualization: UV and iodine
  Rf: 0.64
Solubility: soluble to 2% in water.

EXAMPLE 10

2-[(4-Chlorobenzyloxy)methyl]morpholine hydrogen maleate

In a similar manner, the procedure of Example (1a) being applied to para-chlorobenzyl alcohol, 1-(para-chlorobenzyloxy)-2,3-epoxypropane is obtained. When condensed according to Example (1b) with 2-aminoethyl hydrogen sulfate (ester), this derivative gives the compound of formula:

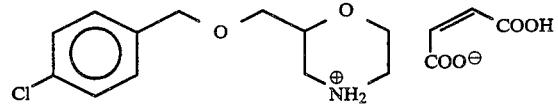

Empirical formula: $C_{16}H_{20}ClNO_6$
Molecular mass: 357.79
Melting point: 106.5° C.
Thin layer chromatography:
  support: silica gel Merck 60 F 254
  solvent: chloroform/methanol/ammonia solution (80:18:2)
  visualization: UV and iodine
  Rf: 0.64
Solubility: soluble to 6% in water.

EXAMPLE 11

2-[(2-Ethoxybenzyloxy)methyl]morpholine hydrogen maleate

In a similar manner, the procedure of Example (1a) being applied to ortho-ethoxybenzyl alcohol, 1-(orthoethoxybenzyloxy)-2,3-epoxypropane is obtained. When condensed with 2-aminoethyl hydrogen sulfate (ester) according to Example (1b), this derivative leads to the compound of formula:

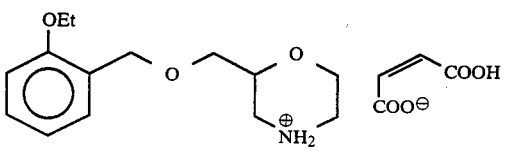

Empirical formula: $C_{18}H_{25}NO_7$
Molecular mass: 367.40
Melting point: 119°–120° C.
Thin layer chromatography:
  support: silica gel Merck 60 F 254
  solvent: chloroform/methanol/ammonia solution (80:18:2)
  visualization: UV and iodine
  Rf: 0.70
Solubility: soluble to 3% in water.

EXAMPLE 12

2-[(2,4-Dichlorobenzyloxy)methyl]morpholine hydrogen maleate

Application of the procedure described in Example (1a) to 2,4-dichlorobenzyl alcohol yields 1-(2,4-dichlorobenzyloxy)-2,3-epoxypropane. The latter, when condensed with 2-aminoethyl hydrogen sulphate according to Example (1b), leads to the derivative of formula:

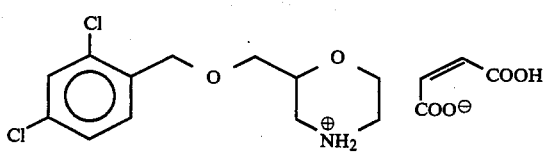

Empirical formula: $C_{16}H_{19}Cl_2N_2O_6$
Molecular mass: 392.23
Melting point: 130.5° C.
Thin layer chromatography:
  support: silica gel Merck 60 F 254
  solvent: chloroform/methanol/ammonia solution (80:18:2)
  visualization: UV and iodine
  Rf: 0.71
Solubility: soluble to 4% in water.

EXAMPLE 13

2-[(3,4-Dichlorobenzyloxy)methyl]morpholine hydrogen maleate

Application of the procedure of Example (1a) to 3,4-dichlorobenzyl alcohol enables 1-(3,4-dichlorobenzyloxy)-2,3-epoxypropane to be prepared. The latter, when condensed with 2-aminoethyl hydrogen sulfate (ester) according to Example (1b), yields the compound of formula:

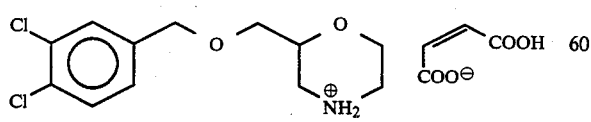

Empirical formula: $C_{16}H_{19}Cl_2N_2O_6$
Molecular mass: 392.23
Melting point: 144° C.
Thin layer chromatography:
  support: silica gel Merck 60 F 254
  solvent: chloroform/methanol/ammonia solution (80:18:2)
  visualization: UV and iodine
  Rf: 0.60
Solubility: soluble to 1% in water.

EXAMPLE 14

2-[(2,6-Dichlorobenzyloxy)methyl]morpholine hydrogen maleate

In a similar manner, the application of the procedure of Example (1a) to 2,6-dichlorobenzyl alcohol gives 1-(2,6-dichlorobenzyloxy)-2,3-epoxypropane. The latter, when condensed according to Example (1b) with 2-aminoethyl hydrogen sulfate, leads to the derivative of formula:

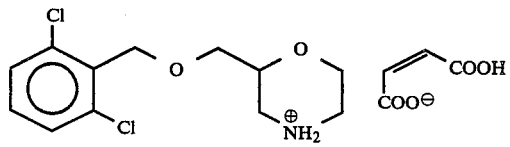

Empirical formula: $C_{16}H_{19}Cl_2NO_6$
Molecular mass: 392.23
Melting point: 140° C.
Thin layer chromatography:
  support: silica gel Merck 60 F 254
  solvent: chloroform/methanol/ammonia solution (80:18:2)
  visualization: UV and iodine
  Rf: 0.65
Solubility: soluble to 5% in water.

EXAMPLE 15

2-[(2-Fluoro-6-chlorobenzyloxy)methyl]morpholine hydrogen maleate

The procedure of Example (1a) being applied to 2-fluoro-6-chlorobenzyl alcohol, 2-(2-fluoro-6-chlorobenzyloxy)-2,3-epoxypropane is obtained. The latter, condensed according to Example (1b) with 2-aminoethyl hydrogen sulfate, leads to the derivative of formula:

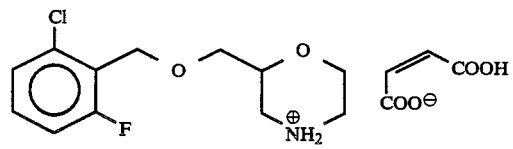

Empirical formula: $C_{16}H_{19}ClFNO_6$
Molecular mass: 375.78
Melting point: 145° C.
Thin layer chromatography:
  support: silica gel Merck 60 F 254
  solvent: chloroform/methanol/ammonia solution (80:18:2)
  visualization: UV and iodine
  Rf: 0.75
Solubility: soluble to 3% in water.

EXAMPLE 16

2-[(3-Phenylpropyloxy)methyl]morpholine hydrogen oxalate

Application of the procedure of Example (1a) to 3-phenylpropyl alcohol yields 1-(3-phenylpropyloxy)-

2,3-epoxypropane. The latter, when condensed according to Example (1b) with 2-aminoethyl hydrogen sulfate, leads, after salification with oxalic acid, to the compound of formula:

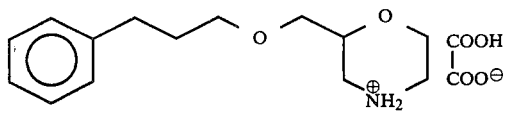

Empirical formula: $C_{16}H_{23}NO_6$
Molecular mass: 325.361
Melting point: 74° C.
Thin layer chromatography:
   support: silica gel Merck 60 F 254
   solvent: chloroform/methanol/ammonia solution (80:18:2)
   visualization: iodine
   Rf: 0.70
Solubility: soluble to 10% in water.

EXAMPLE 17

2-{[(1,4-Benzodioxan-2-yl)methoxy]methyl}morpholine hydrogen maleate

In a similar manner to Example (1a), with benzyl alcohol replaced by (1,4-benzodioxan-2-yl)methanol, 1-[(1,4-benzodioxan-2-yl)methoxy]-2,3-epoxypropane is obtained. The latter derivative, when condensed according to Example (1b) with 2-aminoethyl hydrogen sulfate, leads to the derivative of formula:

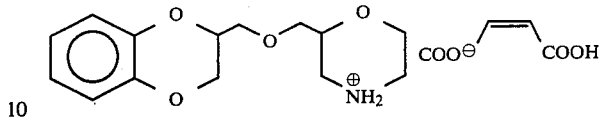

Empirical formula: $C_{18}H_{23}NO_8$
Molecular mass: 381.38
Melting point: 123°–124° C.
Thin layer chromatography:
   support: silica gel Merck 60 F 254
   solvent: chloroform/methanol/ammonia solution (80 18:2)
   visualization: UV and iodine
   Rf: 0.65
Solubility: soluble to 10% in water.

EXAMPLES 18 to 36

In a manner similar to that described in Example 1, with the corresponding alcohols being used, the following 2-substituted morpholine derivatives are prepared:

| Examples N° | Chemical formula | Empirical formula | Molecular mass |
|---|---|---|---|
| 18 | 3-CF₃-C₆H₄-CH₂-O-CH₂-CH(morpholinium)-CH₂-COO⁻ · maleate | $C_{17}H_{20}F_3NO_6$ | 391.34 |
| 19 | 2-NO₂-C₆H₄-CH₂-O-CH₂-CH(morpholinium)-CH₂-COO⁻ · maleate | $C_{16}H_{22}N_2O_8$ | 370.35 |
| 20 | 3-NO₂-C₆H₄-CH₂-O-CH₂-CH(morpholinium)-CH₂-COO⁻ · maleate | $C_{16}H_{22}N_2O_8$ | 370.35 |
| 21 | 4-NO₂-C₆H₄-CH₂-O-CH₂-CH(morpholinium)-CH₂-COO⁻ · maleate | $C_{16}H_{22}N_2O_8$ | 370.35 |
| 22 | 2,4-(MeO)₂-C₆H₃-CH₂-O-CH₂-CH(morpholinium)-CH₂-COO⁻ · maleate | $C_{18}H_{25}NO_8$ | 383.39 |
| 23 | 2,3-(MeO)₂-C₆H₃-CH₂-O-CH₂-CH(morpholinium)-CH₂-COO⁻ · maleate | $C_{18}H_{25}NO_8$ | 383.39 |

-continued

| Examples N° | Chemical formula | Empirical formula | Molecular mass |
|---|---|---|---|
| 24 | 3,4-(MeO)₂-C₆H₃-CH₂-O-CH₂-CH(O-CH₂-CH₂-)-CH₂-NH₂⊕ · ⁻OOC-CH=CH-COOH (maleate) | C₁₈H₂₅NO₈ | 383.39 |
| 25 | 3,5-(MeO)₂-C₆H₃-CH₂-O-CH₂-CH(O-CH₂-CH₂-)-CH₂-NH₂⊕ · ⁻OOC-CH=CH-COOH | C₁₈H₂₅NO₈ | 383.39 |
| 26 | 3,4,5-(MeO)₃-C₆H₂-CH₂-O-CH₂-CH(O-CH₂-CH₂-)-CH₂-NH₂⊕ · ⁻OOC-CH(COOH)- | C₁₇H₂₅NO₉ | 387.38 |
| 27 | C₆H₅-CH₂-CH₂-O-CH₂-CH(O-CH₂-CH₂-)-CH₂-NH₂⊕ · ⁻OOC-CH=CH-COOH | C₁₇H₂₃NO₆ | 337.36 |
| 28 | 2-MeO-C₆H₄-CH₂-CH₂-O-CH₂-CH(O-CH₂-CH₂-)-CH₂-NH₂⊕ · ⁻OOC-CH=CH-COOH | C₁₈H₂₅NO₇ | 367.39 |
| 29 | 3-MeO-C₆H₄-CH₂-CH₂-O-CH₂-CH(O-CH₂-CH₂-)-CH₂-NH₂⊕ · ⁻OOC-CH=CH-COOH | C₁₈H₂₅NO₇ | 367.39 |
| 30 | 4-MeO-C₆H₄-CH₂-CH₂-O-CH₂-CH(O-CH₂-CH₂-)-CH₂-NH₂⊕ · Cl⁻ | C₁₄H₂₂ClNO₃ | 287.79 |
| 31 | 3,4-(MeO)₂-C₆H₃-CH₂-CH₂-O-CH₂-CH(O-CH₂-CH₂-)-CH₂-NH₂⊕ · ⁻OOC-CH=CH-COOH | C₁₉H₂₇NO₈ | 397.41 |
| 32 | 2,5-(MeO)₂-C₆H₃-CH₂-CH₂-O-CH₂-CH(O-CH₂-CH₂-)-CH₂-NH₂⊕ · ⁻OOC-CH=CH-COOH | C₁₉H₂₇NO₈ | 397.41 |

| Examples N° | Chemical formula | Empirical formula | Molecular mass |
|---|---|---|---|
| 33 | ![structure 33] | C₁₅H₂₀ClNO₆ | 345.78 |
| 34 | ![structure 34] | C₁₆H₂₀ClNO₆ | 293.79 |
| 35 | ![structure 35] | C₂₀H₂₇NO₆ | 377.42 |
| 36 | ![structure 36] | C₁₈H₂₃NO₆ | 349.37 |

EXAMPLE 37

2-[(1-Phenylethyloxy)methylmorpholine hydrogen oxalate

A heterogeneous mixture consisting of 300 ml of 50% strength caustic soda and 300 ml of epichlorohydrin containing 5.55 g (0.016 mol) of tetrabutylammonium hydrogen sulfate is stirred vigorously and then treated dropwise with 50 g (0.405 mol) of 1-phenylethanol.

The addition is regulated in such a manner that the internal temperature does not exceed 25°, with immersion, where required, in a cold water bath. After 5 hours' stirring at room temperature, the mixture is treated with ice-cold water.

The organic phase is extracted with ether, washed with water and then with saline water, and dried over sodium sulfate. After filtration, the solution is evaporated to dryness and the residual oil distilled under vacuum.

The fraction boiling between 128° and 134° at 5 mm Hg consists of 1-(1-phenylethyloxy)-2,3-epoxypropane. $n_D^{26} = 1.5038$ (Yld: 85%). The above epoxide (18 g or 0.1 mol), dissolved in 90 ml of methanol, is added to a solution of 45 ml of 40% strength caustic soda which has been treated beforehand for 10 minutes with 155 g (0.8 mol) of 2-aminoethyl hydrogen sulfate (ester). After 1 hour's heating at 55°, a further 45 ml of caustic soda is added, and the mixture is brought for a further 5 hours to the same temperature. The mixture is then taken up in 250 ml of water and extracted with 2×150 ml of toluene.

This organic phase is acidified with 2×150 ml of 2N $H_2SO_4$, the aqueous phase is recovered and the base is then salted out by adding 100 ml of 40% strength caustic soda and extracted with 2×100 ml of toluene. The toluene phase is washed with saline water and then dried over sulfate and evaporated to dryness (m=15 g).

A solution of 7.40 g of oxalic acid in 100 ml of isopropyl alcohol is added to the solution of base in the same solvent. After the mixture is cooled, the organic salt is recovered and recrystallized from boiling isopropyl alcohol to give the derivative of the formula:

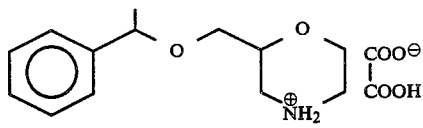

Empirical formula: $C_{15}H_{21}NO_6$
Molecular mass: 311.33
Melting point: 108° C.
Thin layer chromatography:
  support: silica gel Merck 60 F 254
  solvent: chloroform/methanol/ammonia solution (80:18:2)
  visualization: UV and iodine
  Rf 0.62
White crystals, soluble to 5% in water.

EXAMPLES 38 to 41

In a manner similar to that described in Example 37, with the corresponding alcohols and acids being used, the following 2-substituted morpholine derivatives are prepared:

| Examples N° | Chemical formula | Empirical formula | Molecular mass |
|---|---|---|---|
| 38 | MeO-phenyl-CH(CH₃)-O-CH₂-CH(O-CH=C(COO⁻)-)-CH₂-NH₂⁺-CH₂-COOH | $C_{18}H_{25}NO_7$ | 367.39 |
| 39 | MeO-phenyl-CH(CH₃)-O-CH₂-CH(O-CH=C(COO⁻)-)-CH₂-NH₂⁺-CH₂-COOH | $C_{18}H_{25}NO_7$ | 367.39 |
| 40 | MeO-phenyl-CH(CH₃)-O-CH₂-CH(O-CH=C(COO⁻)-)-CH₂-NH₂⁺-CH₂-COOH | $C_{18}H_{25}NO_7$ | 367.39 |
| 41 | Cl-phenyl-CH(CH₃)-O-CH₂-CH(O-CH₂-CH(COOH)(COO⁻))-CH₂-NH₂⁺ | $C_{15}H_{20}ClNO_6$ | 345.78 |

EXAMPLE 42

2-[(4-Hydroxybenzyloxy)methyl]morpholine hydrogen oxalate

(42a) 1-(4-Benzyloxybenzyloxy)-2,3-epoxypropane

To a mixture of 50 ml of epichlorohydrin and 50 ml of 50% strength (by weight) caustic soda containing 630 mg (2 mmol) of tetrabutylammonium hydrogen sulfate in a 500-ml three-necked flask, 10 g (46 mmol) of meta-benzyloxybenzyl alcohol is added in the course of 15 minutes with brisk stirring. After two hours' stirring at 25°–27°, the mixture is poured into cold water and extracted with 3×50 ml of ether. The organic phase is washed with water until neutral, dried over sulfate then evaporated to dryness at up to 50° at 0.1 mm Hg. The residue consists of the pure epoxide.

(42b) 2-[4-Benzyloxybenzyloxy)methyl]morpholine hydrogen oxalate

The procedure of Example 1b being used, with the epoxide described above being condensed with 2-aminoethyl hydrogen sulfate, there is obtained, after salification with oxalic acid, the derivative of formula:

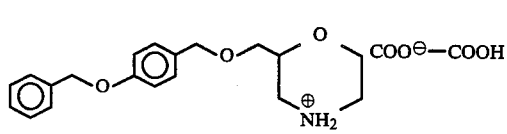

Empirical formula: $C_{21}H_{25}NO_7$
Molecular mass: 403.431
Melting point: 124° C.
Thin layer chromatography:
  support: silica gel Merck 60 F 254
  solvent: chloroform/methanol/ammonia solution (80:18:2)
  visualization: UV and iodine
  Rf: 0.68
White crystals, soluble to 1% in water.
Yield: 40%.

(42c) 2-[(4-Hydroxybenzyloxy)methyl]morpholine hydrogen oxalate

A solution of 10 g (24.8 mmol) of 2-[(4-benzyloxybenzyloxy)methyl]morpholine hydrogen oxalate in 150 ml of ethanol and containing 2 g of palladium on charcoal (5% Pd) is hydrogenated until the theoretical amount of hydrogen has been completely absorbed.

The hydrogenolysis takes place in approximately 2 hours.

The mixture is then purged with nitrogen, the catalyst is removed by filtration on silica paper and the filtrate is then evaporated to dryness.

The residual solid is taken up in the minimum quantity of a boiling mixture of isopropyl alcohol and ethyl acetate. The product is allowed to crystallize slowly overnight at room temperature. The crystals of organic salt are recovered by filtration, and have the formula:

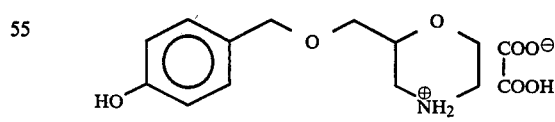

Empirical formula: $C_{14}H_{19}NO_7$
Molecular mass: 313.30
Thin layer chromatography:
  support: silica gel Merck 60 F 254
  solvent: chloroform/methanol/ammonia solution (80:18:2)
  visualization: UV and iodine
  Rf: 0.50
Solubility: soluble to 20% in water.

EXAMPLE 43

2-[(3-Hydroxybenzyloxy)methyl]morpholine hydrogen oxalate

The compound of formula:

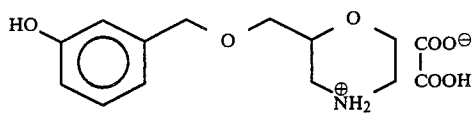

is obtained by working in the same manner as described in Example 42.

Empirical formula: $C_{14}H_{19}NO_7$
Molecular mass: 313.30
Thin layer chromatography:
  support: silica gel Merck 60 F 254
  solvent: chloroform/methanol/ammonia solution (80:18:2)
  visualization: UV and iodine
  Rf: 0.50
Solubility: soluble to 10% in water.

EXAMPLE 44

2-[(4-Aminobenzyloxy)methyl]morpholine dihydrogen succinate

A solution of 10 g (37 mmol) of 2-[(4-nitrobenzyloxy)methyl]morpholine hydrogen succinate in 200 ml of methanol is hydrogenated at atmospheric pressure in the presence of 1 g of palladium on charcoal (10% Pd). When the theoretical amount of hydrogen has been absorbed, the mixture is purged with nitrogen and the catalyst is filtered off on a silica paper and rinsed with methanol. The filtrate is evaporated to dryness. The residue is taken up in the minimum of methanol and then added to a boiling solution of succinic acid in ethyl acetate. Crystallization is primed with a rod and the mixture is then allowed to return slowly to room temperature during 24 hours, the crystals of organic salt are filtered off and washed with a little ethyl acetate; they correspond to the following formula:

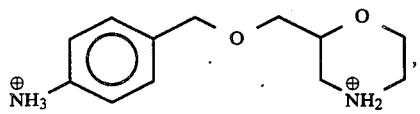

Empirical formula: $C_{20}H_{30}N_2O_{10}$
Molecular mass: 458.46
Thin layer chromatography:
  support: silica gel Merck 60 F 254
  solvent: chloroform/methanol/ammonia solution (80:18:2)
  visualization: UV and iodine
  Rf: 0.55
Soluble in water to 6%.

EXAMPLE 45

2-[(3-Aminobenzyloxy)methyl]morpholine dihydrogen succinate

In a manner similar to that described in Example 44, the derivative of formula:

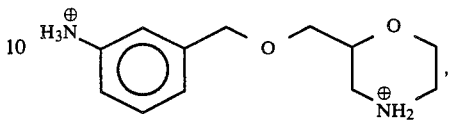

is obtained.

Empirical formula: $C_{20}H_{30}N_2O_{10}$
Molecular mass: 458.46
Thin layer chromatography:
  support: silica gel Merck 60 F 254
  solvent: chloroform/methanol/ammonia solution (80:18:2)
  visualization: UV and iodine
  Rf: 0.57
Soluble to 12% in water.

EXPERIMENTS (a) Toxicology

The chemical compounds described above were subjected to toxicity checks.

This study was performed on ordinary mice weighing 20 to 22 grams.

The substances were administered orally.

The $LD_{50}$ is calculated according to the method of KARBER, 1931, Arch. Pathol. Pharmacol., 162, 480.

All the $LD_{50}$ values observed fall between 300 and 2,000 mg/kg.

(b) Pharmacological study

The pharmacological experiments to which the chemical molecules which are the subject of the present invention were subjected enabled a useful activity on the CNS to be demonstrated.

(1) As a guide, the compounds of Examples 3, 5, 8, 9, 11 and 16 will be mentioned in respect of their activity in the 5-HTP (5-hydroxytryptophan) potentiation test according to the method of Christensen A. V. et al., 1977, Eur. J. Pharmacol., 41, 153-162.

The mice receive an intravenous injection of 5-HTP (100 mg/10 ml/kg) after oral administration of the compounds to be studied (25 ml/kg). Fifteen minutes after the injection of 5-HTP, the presence and intensity of head movements and tremors are noted.

The results are shown in the table below. Quipazine, which is used as a reference product in this text, has an $ED_{50}$ of 15 mg/kg.

| PRODUCTS | $ED_{50}$ (mg/kg) |
|---|---|
| Example 3 | 10 |
| Example 5 | 16 |
| Example 8 | 15 |
| Example 9 | 15 |
| Example 11 | 15 |
| Example 14 | 18 |
| Quipazine | 15 |

(2) All the examples of the present invention prove to be inactive in the 5-HT (5-hydroxytryptamine) uptake test according to the method of LANGER et al. (1980, Science, 210, 1133-1135). This suggests an indirect mechanism of action, favoring the serotoninergic system.

(3) It should also be noted that some examples of the present invention possess useful analgesic activity in the heating-plate test (WOOLFE G. and MacDONALD A. D. 1944, J. Pharmacol. Exp. Ther., 80, 300).

The products to be tested are administered to the mouse orally. 30 minutes later, the mice are placed on a plate brought to 65° C. The nociceptive reactions are assessed objectively in terms of the licking of the forepaws. The time for this response to appear is noted.

The method of calculation used is that described by HARRIS L. S. and PIERSON A. K. (1964, J. Pharmacol. Exp. Ther., 143, 141-148).

Dextropropoxyphene, used as a reference product in this test, shows a degree of analgesia of 15%.

| PRODUCTS (100 mg/kg) | PERCENTAGE ANALGESIA |
|---|---|
| Example 5 | 20 |
| Example 9 | 16 |
| Example 11 | 16 |
| Example 14 | 23 |
| Dextropropoxyphene | 15 |

(c) Therapeutic applications

In the light of their pharmacological properties and low toxicity, these compounds can be used in therapy in the treatment of disorders of the central nervous system and also in the treatment of various painful conditions.

Among the compounds of the present invention, the products which have shown the most conclusive results are those of Examples 1, 3, 4, 5, 6, 7, 8, 9, 10, 11, 12, 14 and 15.

The compounds of general formula I according to the present invention, and their addition salts with therapeutically compatible acids, can thus be used as drugs, for example in the form of pharmaceutical preparations which are adapted to facilitate bioavailability.

These preparations can take solid form, for example tablets, dragées, capsules or gelatin capsules, or liquid form (solutions, suspensions or emulsions). The pharmaceutical preparations in a suitable form for injection are subjected to classical pharmaceutical procedures such as sterilization, and/or can contain adjuvants (eg. preservatives, wetting or emulsifying stabilizers, buffer tablets, and the like).

The dosages at which the active compounds and their addition salts can be administered can vary to a large extent, depending on the state of the patient. A daily dosage of approximately 0.1 to 5 mg/kg of body weight is, however, preferable.

The pharmaceutical compositions according to the invention can be used in human and veterinary medicine, and more especially in the treatment of neurotic and reactive depressive states of various kinds (depression, anorexia, sleep disorders, and the like), as well as in the treatment of various painful phenomena.

Other active principles can be combined with the compounds of general formula I according to the invention to complement or reinforce their therapeutic effects within one and the same pharmaceutical composition.

The present invention is naturally not limited to the particular examples mentioned simply as a guide, but it is entirely possible, without thereby departing from the scope of the invention, to conceive of a number of variants and modifications thereof.

We claim:

1. 2-(Arylalkyloxymethyl)morpholine derivatives corresponding to the general formula (I):

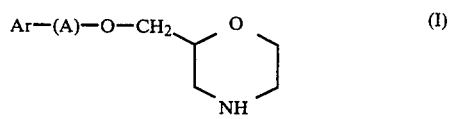

in which:

Ar denotes an aromatic group, and more especially the following radicals:

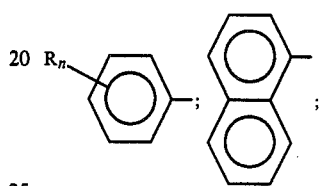

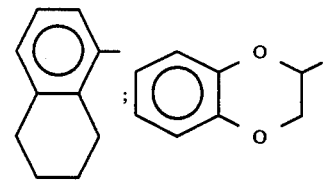

in the case where Ar denotes a phenyl radical, R denotes a hydrogen atom, an alkyl, alkoxy or halogen group, a trifluoromethyl radical, a nitro or amino group, a hydroxy group or an arylalkyloxy group, n denotes the values 1 to 3;

in the case where n=2 or 3, the radicals R can be identical or different, or can form a methylenedioxy or 1,2-ethylenedioxy group; and A denotes a linear or branched alkylene radical having 1 to 4 carbon atoms or an alkenylene radical having 2 to 3 carbon atoms, as well as the salts thereof with therapeutically acceptable inorganic or organic acids.

2. Compounds corresponding to the general formula I as claimed in claim 1, which compounds are chosen from:

2-(benzyloxymethyl)morpholine hydrogen maleate

2-[(2-methoxybenzyloxy)methyl]morpholine hydrogen fumarate

2-[(3-methoxybenzyloxy)methyl]morpholine hydrogen maleate

2-[(4-methoxybenzyloxy)methyl]morpholine hydrogen oxalate

2-[(2-methylbenzyloxy)methyl]morpholine hydrogen maleate

2-[(3-methylbenzyloxy)methyl]morpholine hydrogen maleate

2-[(4-methylbenzyloxy)methyl]morpholine hydrogen oxalate

2-[(2-chlorobenzyloxy)methyl]morpholine hydrogen maleate

2-[(3-chlorobenzyloxy)methyl]morpholine hydrogen maleate

2-[(4-chlorobenzyloxy)methyl]morpholine hydrogen maleate
2-[(2-ethoxybenzyloxy)methyl]morpholine hydrogen maleate
2-[(2,4-dichlorobenzyloxy)methyl]morpholine hydrogen maleate
2-[(3,4-dichlorobenzyloxy)methyl]morpholine hydrogen maleate
2-[(2,6-dichlorobenzyloxy)methyl]morpholine hydrogen maleate
2-[(2-fluoro-6-chlorobenzyloxy)methyl]morpholine hydrogen maleate
2-[(3-phenylpropyloxy)methyl]morpholine hydrogen oxalate
2-{[(1,4-oenzodioxan-2-yl)methoxy]methyl}morpholine hydrogen maleate
2-[(3-trifluoromethylbenzyloxy)methyl]morpholine hydrogen maleate
2-[(2-nitrobenzyloxy)methyl]morpholine hydrogen succinate
2-[(3-nitrobenzyloxy)methyl]morpholine hydrogen succinate
2-[(4-nitrobenzyloxy)methyl]morpholine hydrogen succinate
2-[(2,4-dimethoxybenzyloxy)methyl]morpholine hydrogen maleate
2-[(2,3-dimethoxybenzyloxy)methyl]morpholine hydrogen maleate
2-[(3,4-dimethoxybenzyloxy)methyl]morpholine hydrogen maleate
2-[(3,5-dimethoxybenzyloxy)methyl]morpholine hydrogen maleate
2-[(3,4,5-trimethoxybenzyloxy)methyl]morpholine hydrogen oxalate
2-[(2-phenylethyloxy)methyl]morpholine hydrogen maleate
2-{[2-(2-methoxyphenyl)ethyloxy]methyl}morpholine hydrogen maleate
2-{[2-(3-methoxyphenyl)ethyloxy]methyl}morpholine hydrogen maleate
2-{[2-(4-methoxyphenyl)ethyloxy]methyl}morpholine hydrochloride
2-{[2-(3,4-dimethoxyphenyl)ethyloxy]methyl}morpholine hydrogen maleate
2-{[2-(2,5-dimethoxyphenyl)ethyloxy]methyl}morpholine hydrogen fumarate
2-{[2-(2-chlorophenyl)ethoxy]methyl}morpholine hydrogen oxalate
2-[(1-naphthyl)methoxymethyl]morpholine hydrochloride
2-[(5,6,7,8-tetrahydro-1-naphthyl)methoxymethyl]morpholine hydrogen maleate
2-(cinnamyloxymethyl)morpholine hydrogen maleate
2-[(1-phenylethoxy)methyl]morpholine hydrogen oxalate
2-{[1-(2-methoxyphenyl)ethoxy]methyl}morpholine hydrogen maleate
2-{[1-(3-methoxyphenyl)ethoxy]methyl}morpholine hydrogen maleate
2-{[1-(2-chlorophenyl)ethyloxy]methyl}morpholine hydrogen oxalate
2-{[1-(4-methoxyphenyl)ethyloxy]methyl}morpholine hydrogen maleate
2-[(4-hydroxybenzyloxy)methyl]morpholine hydrogen oxalate
2-[(4-benzyloxybenzyloxy)methyl]morpholine hydrogen oxalate
2-[(3-hydroxybenzyloxy)methyl]morpholine hydrogen oxalate
2-[(3-benzyloxybenzyloxy)methyl]morpholine hydrogen oxalate
2-[(3-aminobenzyloxy)methyl]morpholine dihydrogen succinate
2-[(4-aminobenzyloxy)methyl]morpholine dihydrogen succinate.

3. Pharmaceutical compositions which contain as active principle at least one compound as claimed in any one of claims 1 and 2 in association with a pharmaceutically acceptable adjuvant.

* * * * *